United States Patent [19]
Kawamura et al.

[11] Patent Number: 4,926,006
[45] Date of Patent: May 15, 1990

[54] ALUMINOBOROSILICATE CONTAINING ALKALINE EARTH METAL, A METHOD FOR THE PREPARATION THEREOF AND A METHOD FOR THE CATALYTIC PREPARATION OF A LOWER OLEFIN THEREWITH

[75] Inventors: Kichinari Kawamura, Tsuchiura; Yasuo Kono, Tokuyama; Hideo Okado, Ushiku; Shigemitsu Shin, Yatabe; Haruo Takaya, Abiko, all of Japan

[73] Assignee: Director General of Agency of Industrial Science and Technology, Tokyo, Japan

[21] Appl. No.: 221,109

[22] Filed: Jul. 19, 1988

Related U.S. Application Data

[62] Division of Ser. No. 925,724, Oct. 30, 1986, abandoned.

[51] Int. Cl.$^5$ ............................................... C07C 1/00
[52] U.S. Cl. ................................................... 585/640
[58] Field of Search ......................................... 585/640

[56] References Cited
U.S. PATENT DOCUMENTS
4,767,886  8/1988  Kawamura ........................ 585/640

Primary Examiner—Curtis R. Davis
Attorney, Agent, or Firm—Hopgood, Calimafde, Kalil, Blaustein & Judlowe

[57] ABSTRACT

The aluminoborosilicate containing an alkaline earth metal element, e.g. calcium, characterized by the chemical composition and the X-ray diffraction pattern is prepared by the hydrothermal reaction of a reaction mixture containing the source materials of boron and the alkaline earth in a similar procedure to that for the preparation of ZSM-5 type zeolites. Different from the conventional ZSM-5 zeolites into which calcium ions are introduced by ion exchange, the calcium ions in the inventive aluminoborosilicate are not replaceable by ion exchange with protons or alkali metal ions. The aluminoborosilicate of the invention after conversion into the hydrogen form is an excellent catalyst for the conversion of methyl alcohol or dimethyl ether into lower olefins such as ethylene and propylene in respect of the selectivity and durability of the catalytic activity with remarkably decreased deposition of carbonaceous materials.

4 Claims, 1 Drawing Sheet

ALUMINOBOROSILICATE CONTAINING ALKALINE EARTH METAL, A METHOD FOR THE PREPARATION THEREOF AND A METHOD FOR THE CATALYTIC PREPARATION OF A LOWER OLEFIN THEREWITH

This is a divisional of co-pending application Ser. No. 925,724 filed on Oct. 30, 1986, and now abandoned.

BACKGROUND OF THE INVENTION

The present invention relates to a novel aluminoborosilicate containing an alkaline earth metal, a method for the preparation thereof and a method for the catalytic preparation of a lower olefin using the same as the catalyst. More particularly, the invention relates to a novel microcrystalline zeolite having a specific crystalline structure useful as a catalyst for the gas-phase preparation of lower olefins, such as ethylene and propylene an efficient method for the preparation of such a novel microcrystalline zeolite and an efficient method for the preparation of a lower olefin using the microcrystalline zeolite as the catalyst.

As is known, one of the world-wide issues of importance in recent years is the problem of exhaustion of the petroleum resources and this problem is especially serious in countries having no or little source of petroleum such as Japan. Accordingly, it is eagerly desired to develop an efficient method for the utilization of coals, natural gases and the like as a substitute of petroleum. For example, it would be very desirable to establish an industrially feasible method for the synthetic preparation of olefins, paraffins, aromatics and the like from methane and carbon monoxide via methyl alcohol. Most of such processes are performed by the catalytic gas-phase reaction using a solid catalyst and various types of zeolites or crystalline aluminosilicates and related materials have been proposed as a catalyst therefor.

A variety of zeolitic crystalline aluminosilicates occur in nature but most of the catalytically useful zeolites are synthetically prepared. Synthetically prepared zeolites have a well-controlled crystalline structure with a large number of interstices and tunnel-like pores therein to serve as a so-called molecular sieve capable of adsorbing only molecules of adsorbates having a dimension smaller than a certain upper limit. The configuration and dimension of the interstices and pores are determined by the manner in which the units of $SiO_2$ and $Al_2O_3$ in the crystalline structure are covalently bonded together possessing the oxygen atoms in common. The electric neutrality of the tetrahedron containing the aluminum atom is maintained usually with alkali metal ions or, in particular, ions of sodium and/or potassium.

Zeolitic crystalline aluminosilicates are usually prepared by the hydrothermal reaction under normal or superatmospheric pressure of an aqueous reaction mixture containing the source materials of silica, alumina and alkali metal ions. The basic compound added to the reaction mixture may be an organic nitrogen compound or an organic phosphorus compound so as to give a zeolite product having specifically modified adsorption characteristics and catalytic activity. For example, the ZSM-type zeolites are prepared by use of an organic basic compound such as tetraalkyl ammonium compounds, tetraalkyl phosphonium compounds, pyrrolidine, ethylene diamine, choline and the like and are highlighted in recent years in respect of their very unique adsorptivity and catalytic activity. In particular, the ZSM-5 zeolite has pores of a medium pore diameter of 5 to 6 Å to exhibit specific adsorptivity by which linearly chained or slightly branched hydrocarbon molecules can be adsorbed thereon but highly branched hydrocarbon molecules cannot be adsorbed. It is reported in Japanese Patent Kokai No. 52-43800 that the ZSM-5 type zeolite can be synthesized by the hydrothermal reaction of an aqueous reaction mixture containing the source materials of silica, alumina and alkali metal ions in combination with tetra(n-propyl) ammonium compound as the organic base.

The synthetic process for the preparation of hydrocarbons from methyl alcohol and/or dimethyl ether as the starting material is under extensive and intensive investigations in recent years. The reaction is usually performed by use of a so-called solid acid catalyst and the subject matters of many patent publications have been various kinds of zeolites, heteropolyacids and the like useful therefor. For example, the above mentioned ZSM-5 type zeolite exhibits excellent catalytic performance in the synthetic process for the preparation of hydrocarbons mainly composed of the gasoline fraction having up to 10 carbon atoms in a molecule from methyl alcohol as the starting material in respect of the stability of the catalytic activity and the catalyst life. A problem in the use of this type of the solid catalyst is the relatively low selectivity for the formation of lower olefins such as ethylene and propylene. On the other hand, a high selectivity for the formation of ethylene and propylene in the same reaction as above can be obtained by using a zeolite of another type ZSM-34 as the catalyst although the zeolite of this type is practically not feasible because of the rapid decrease of the catalytic activity at high temperatures due to the deposition of carbonaceous materials thereon.

Accordingly, it is a very important problem in this technical field of chemical industry to provide a solid catalyst capable of exhibiting excellent catalytic performance including a high selectivity for the formation of lower olefins and a long catalytic life even at high temperatures without decrease in the catalytic activity due to the deposition of carbonaceous materials.

SUMMARY OF THE INVENTION

It is therefore an object of the present invention to provide a novel solid catalyst capable of overcoming the above mentioned problems and disadvantages in the prior art catalysts and to provide a method for the preparation of such a solid catalyst as well.

Another object of the invention is to provide a method for the catalytic preparation of lower olefins from methyl alcohol and/or dimethyl ether with a high selectivity by using the thus obtained solid catalyst.

Thus, the solid catalyst provided by the invention is a crystalline aluminoborosilicate containing an alkaline earth metal represented by the formula $$aM^1_2O.bM^2O.Al_2O_3: dB_2O_3.cSiO_2.nH_2O, \qquad (I)$$

in which $M^1$ is a monovalent atom selected from the group consisting of a hydrogen atom and atoms of alkali metals, $M^2$ is an atom of an alkaline earth metal, a is zero or a positive number not exceeding 2, b is a positive number in the range from 0.1 to 100, c is a positive number in the range from 12 to 3000, d is a positive number in the range from 0.06 to 120 and n is zero or a positive number not exceeding 30, and characterized by an X-ray diffraction diagram having diffraction lines of strong intensity corresponding to the lattice constants of 11.15±0.15 and 3.84±0.07, diffraction lines of medium intensity corresponding to the lattice constants of 10.01±0.15, 3.81±0.07, 3.74±0.07 and 3.70±0.07 and diffraction lines of weak intensity corresponding to the lattice constants of 7.42±0.10, 6.70±0.10, 6.35±0.10, 5.97±0.10, 5,67±0.10 5.56±0.10, 5.34±0.10, 5.00±0.10, 4.59±0.10, 4.34±0.10, 4,24±0.10, 3.99±0.10, 3.65±0.07, 3.45±0.05, 3.42±0.05, 3.30±0.05, 3.24±0.05, 3.04±0.05, 2.97±0.05, 2.01±0.02 and 1.99±0.02, each lattice constant being in the angstrom unit.

The method of the present invention for the preparation of the above defined crystalline aluminoborosilicate containing an alkaline earth metal utilizes a hydrothermal reaction which comprises heating, at a temperature in the range from 80° to 250° C., an aqueous mixture comprising source materials of silica, alumina, boron oxide and alkali and alkaline earth oxides and a tetrapropyl ammonium compound in such proportions that the molar ratio of $SiO_2:Al_2O_3$, is in the range from 10 to 3000, the molar ratio of $SiO_2:B_2O_3$ is in the range from 1 to 1000, the molar ratio of $OH^-:SiO_2$ is in the range from 0.02 to 10, the molar ratio of $H_2O:SiO_2$ is in the range from 1 to 2000, the molar ratio of the tetrapropyl ammonium compound to $SiO_2$ is in the range from 0.01 to 3 and the atomic ratio of the alkaline earth metal to aluminum is in the range from 0.03 to 300.

Further, the method of the invention for the preparation of a lower olefin comprises contacting a gaseous starting material selected from the group consisting of methyl alcohol, dimethyl ether and mixtures thereof with a crystalline aluminoborosilicate containing an alkaline earth metal defined above.

DETAILED DESCRIPTION OF THE PREFERRED EMBODIMENTS

Figure 1:
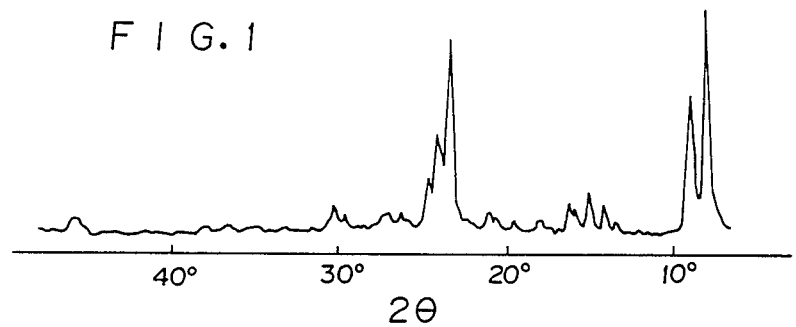
FIG. 1 is an X-ray diffraction diagram of the inventive calcium-containing aluminoborosilicate in the Na-form obtained in Preparation 1.

As is understood from the above given summary of the invention, the alkaline earth-containing aluminoborosilicate of the invention is characterized by the chemical composition expressed relative to the proportions of the oxide constituents as given by the formula (I) and also by the specific X-ray diffraction lines appearing in the X-ray diffraction diagram corresponding to the specific lattice constants. To explain it in more detail, the inventors have continued extensive investigations with the above described objects and arrived at a discovery that, when a boron compound and a salt of an alkaline earth metal are added to the aqueous reaction mixture containing the source materials of silica, alumina and alkali metal ions in the hydrothermal reaction for the preparation of a zeolite, the resultant zeolite may contain the alkaline earth metal in such a large amount as not to be expected in the conventional method of ion exchange and also exhibit a very specific X-ray diffraction pattern ascribable to the microcrystalline skeleton with substitution of the boron atoms and also that this novel zeolitic aluminoborosilicate is useful as a catalyst for the catalytic preparation of lower olefins from methyl alcohol and/or dimethyl ether.

Namely, it is already known that various kinds of zeolitic crystalline aluminosilicates can be modified by incorporating ions of an alkaline earth metal in order to be imparted with improved catalytic properties. A most conventional method for the incorporation of alkaline earth metal ions to a crystalline aluminosilicate is the method of ion exchange of the alumino-silicate in the proton($H+$)-form with ions of the alkaline earth metal to be supported thereon. This method of ion exchange is, however, not satisfactory when it is desired to incorporate a large amount of the alkaline earth metal ions into the crystalline aluminosilicate if not to mention the laboriousness and economical disadvantage of the method.

The present invention has been completed, on the contrary, on the base of the unexpected discovery that, when a compound of an alkaline earth metal is added to the reaction mixture in the hydrothermal synthesis of a crystalline aluminosilicate, the alkaline earth metal ions can readily be incorporated into the crystalline structure of the aluminosilicate in a large amount over the isoelectric amount relative to the aluminum and that such a microcrystalline zeolite is very useful as a catalyst for the catalytic preparation of lower olefins in respect of the selectivity for the formation of ethylene and propylene by conversion from methyl alcohol or dimethyl ether and the durability of the catalyst activity with great decrease in the formation of carbonaceous materials.

The above mentioned discovery is surprising in view of the general understanding in the prior art that addition of a salt of an alkaline earth metal to the reaction mixture of the hydrothermal reaction may have an adverse effect of disturbing the orientation of the crystalline lattices to inhibit the growth of the crystalline structure eventually resulting in an amorphous product. This problem can be solved according to the discovery of the inventors when a tetrapropyl ammonium compound is used as a crystallization moderator in the reaction mixture of which the molar ratio of $SiO_2:Al_2O_3$ is markedly larger than in the conventional hydrothermal process for the preparation of the ZSM-5 type crystalline aluminosilicates even when the reaction mixture under the hydrothermal reaction contains large amounts of a boron compound and salt of alkaline earth metal. Namely, such large amounts of the boron compound and salt of alkaline earth metal have little influence on the crystal growth of the crystalline aluminosilicate and the thus obtained alkaline earth-containing crystalline aluminoborosilicate may exhibit unexpectedly high performance as a catalyst in the catalytic reaction of the subject matter.

The alkaline earth-containing crystalline aluminoborosilicate of the invention is distinguished from conventional zeolites having a pore diameter of 5 to 6 Å and characterized by the chemical composition expressed by the above given formula (I) and the specific pattern of the X-ray diffraction diagram having diffraction lines of strong, medium and weak intensities corresponding to the specific lattice constants, in which the strong, medium and weak intensities mean that the intensity of a particular diffraction line is in the range from 100 to 70%, from 70 to 40% and less than 40%, respectively, of the intensity of the diffraction line corresponding to a lattice constant of 11.15±0.15 Å. The chemical composition expressed by the formula (I) is distinguishable from that of the conventional crystalline aluminosilicates by the features that the molar ratio of $SiO_2:Al_2O_3$ and the atomic ratio of the alkaline earth metal to aluminum are each considerably larger than in the conventional products. Although such an alkaline earth-containing aluminoborosilicate may be prepared by several different synthetic methods, the most advantageous is the method described in the summary of the invention in respect of the performance as a catalyst for the particular catalytic reaction. Namely, the method of the invention can be distinguished over conventional methods by the features that the reaction mixture for the hydrothermal reaction essentially contains specified amounts of a boron compound and a salt of an alkaline earth metal as the sources of the oxides of boron and alkaline earth metal.

In performing the hydrothermal reaction for the synthetic preparation of the crystalline aluminosilicate, the reaction mixture should contain, in addition to the ordinary source materials for silica, alumina and alkali metal ions, specified amounts of a boron compound and a salt of an alkaline earth metal, preferably, in combination with a crystallization moderator which may be an organic amine or, in particular, a tetrapropyl ammonium compound.

The source material of silica suitable for use in the inventive method for the preparation of the crystalline aluminoborosilicate is exemplified by water glass, silica sol, colloidal silica, silica gel, fine powder of silica and the like, of which water glass and colloidal silica are preferred. The source material for alumina is exemplified by sodium aluminate, aluminum nitrate, aluminum sulfate, alumina sol, powdery alumina and the like, of which sodium aluminate, aluminum nitrate and aluminum sulfate are preferred.

The boron compound as the source material of boron oxide constituent in the crystalline aluminoborosilicate is exemplified by boric acid, ammonium borate, potassium borate, sodium borate, calcium borate, boron oxide and the like. The source material of the alkali metal oxide is exemplified by the sodium oxide constituent in water glass, sodium aluminate, sodium hydroxide, potassium hydroxide, sodium chloride, potassium chloride and the like.

The source material of the alkaline earth metal ions is exemplified by organic salts, e.g. acetates and propionates, and inorganic salts, e.g. chlorides and nitrates, of alkaline earth metals. The alkaline earth metals include magnesium, calcium, strontium and barium, of which calcium and strontium are preferred with less preference of magnesium and still less preference of barium. It should be noted that a barium-containing crystalline aluminoborosilicate of the invention can be activated only by a heat treatment at a markedly higher temperature than for the other alkaline earth metals. Particular examples of the alkaline earth metal compound suitable for use include magnesium acetate, magnesium chloride, magnesium nitrate, calcium acetate, calcium chloride, calcium nitrate, strontium acetate, strontium chloride, strontium nitrate, barium acetate, barium chloride, barium nitrate and the like. These alkaline earth metal compounds can be used either singly or as a combination of two kinds or more according to need.

The tetrapropyl ammonium compound as the crystallization moderator is exemplified by tetra(n-propyl) ammonium chloride, tetra(n-propyl) ammonium bromide, tetra(n-propyl) ammonium iodide, tetra(n-propyl) ammonium hydroxide and the like, of which tetra(n-propyl) ammonium bromide is particularly preferred. A mixture of tri(n-propyl) amine and n-propyl bromide can also be used as a substitute for tetra(n-propyl) ammonium bromide.

The aqueous reaction mixture to be subjected to the hydrothermal reaction should be formulated using the above described source materials for the respective constituents of the product and the crystallization moderator to satisfy the following molar ratios or atomic ratio: the molar ratio of silica to alumina $SiO_2:Al_2O_3$ should be in the range from 10 to 3000 or, preferably, from 40 to 1000; the molar ratio of silica to boron oxide $SiO_2:B_2O_3$ should be in the range from 1 to 1000 or, preferably, from 1 to 100; the molar ratio of the hydroxy ions excepting those originating in the organic base to silica $OH^-:SiO_2$ should be in the range from 0.02 to 10 or, preferably, from 0.05 to 0.5; the molar ratio of the tetrapropyl ammonium compound to silica $SiO_2$ should be in the range from 0.01 to 3 or, preferably, from 0.02 to 0.4; and the atomic ratio of the alkaline earth metal to aluminum should be in the range from 0.03 to 300 or, preferably, from 0.4 to 8. The reaction mixture should have an alkalinity of the pH not exceeding 11 so that the reaction mixture prepared by the addition of the above mentioned source materials and crystallization moderator should be further admixed with an acid, e.g. sulfuric, hydrochloric and nitric acids, or an alkali, e.g. alkali metal hydroxides, so as to have an appropriate value of pH.

The hydrothermal reaction is performed by heating the thus prepared aqueous reaction mixture at a temperature in the range from 80° to 250° C. or, preferably, from 150° to 180° C. with agitation under normal pressure or a superatmospheric pressure for a length of time, usually, from 1 to 200 hours or, preferably, from 5 to 50 hours. The reaction product is separated and recovered from the reaction mixture after the reaction by filtration or centrifugal separation, thoroughly washed with water to be freed of the extraneous ionic matters, dried and calcined to give the desired alkaline earth-containing crystalline aluminoborosilicate.

The thus obtained product is an alkaline earth-containing crystalline aluminoborosilicate, of which the alkali metal ions and alkaline earth metal ions are susceptible to ion exchange by a conventional method. Namely, the product can be converted into a crystalline aluminoborosilicate of the so-called proton(H+)-form by the ion-exchange using an inorganic acid, e.g. hydrochloric, sulfuric and nitric acids, or organic acid, e.g. formic and acetic acids, or by the ion-exchange with an ammonium compound into the ammonium-form followed by calcination. It should be noted here that all, if so desired, of the alkali metal ions can readily be replaced with protons while the ion-exchange of the alkaline earth metal ions with protons can proceed with difficulty only to a limited extent. This is a very noticeable characteristic of the inventive crystalline aluminoborosilicate to distinguish the same from conventional crystalline aluminosilicate into which alkaline earth metal ions have been incorporated by the subsequent ion-exchange.

Conventional aluminosilicates modified with alkaline earth metals are prepared by introducing the alkaline earth metal ions into an aluminosilicate of the hydrogen form or alkali metal form by ion exchange and the thus introduced alkaline earth metal ions can be replaced reversibly with protons or alkali metal ions. This is a great difference of the conventional alkaline earth-modified aluminosilicate from the inventive product of which the alkaline earth metal ions are, though not entirely, not replaceable with protons or alkali metal ions. In other words, at least a part of the alkaline earth metal ions in the inventive aluminoborosilicate is bonded to the crystalline structure of the aluminoborosilicate more strongly than the alkaline earth metal ions in conventional alkaline earth-modified aluminosilicates. This unique feature is another characteristic by which the inventive aluminoborosilicate having a pore diameter distribution of 5 to 6 Å can be distinguished from conventional products besides the characteristics of the chemical composition expressed by the formula (I) and the X-ray diffraction pattern.

The inventive alkaline earth-containing aluminoborosilicate can adsorb paraffins of a linearly chained or slightly branched molecular structure such as n-hexane, 3-methyl pentane and the like but has no adsorptivity for 2,2-dimethyl butane among the hexane isomers. The pore diameter and the capacity of adsorption are approximately the same as the conventional ZSM-5 type zeolites.

When the alkaline earth-containing crystalline aluminoborosilicate of the invention is to be used as a catalyst in the reaction for the preparation of lower olefins from methyl alcohol and/or dimethyl ether, the aluminoborosilicate is usually converted in advance into the hydrogen form by replacing all or most of the alkali metal ions and a part of the alkaline earth metal ions with protons. This replacement of ions can be performed by any known method of ion exchange. For example, the aluminoborosilicate is first treated with an aqueous solution of an ammonium compound, such as ammonium chloride, to be converted by the replacement of the alkali metal ions with ammonium ions into the ammonium form which is then calcined to decompose the ammonium ions to liberate ammonia leaving hydrogen ions. Alternatively, the alkali metal ions can be replaced directly with protons by the treatment of the aluminoborosilicate with an aqueous solution of an acid such as hydrochloric acid. The aluminoborosilicate after the ion exchange with an aqueous solution of an ammonium salt or acid should be thoroughly washed with water, dried and calcined, for example, at a temperature in the range from 300° to 700° C. for 1 to 100 hours.

As is already mentioned, the alkali metal ions in the inventive aluminoborosilicate can be entirely or mostly ion-exchangeable with protons while most of the alkaline earth metal ions are retained within the crystalline structure even after the ion-exchange treatment to impart the inventive aluminoborosilicate with very specific performance as a catalyst distinguishable from conventional products into which the alkaline earth metal ions have been introduced subsequently by ion exchange.

Following is a description of the process for the preparation of a lower olefin from methyl alcohol and/or dimethyl ether using the above described alkaline earth-containing aluminoborosilicate as the catalyst. Although the aluminoborosilicate in a powdery form can be used as such as the catalyst, it is optional that the aluminoborosilicate powder is shaped into pellets or granules with admixture of a suitable carrier material such as clay, kaolin, silica, alumina, silica-alumina and the like according to need. It is noted that the inventive aluminoborosilicate has catalytic activity not only in the above mentioned preparation of lower olefins but also in the reactions of cracking, isomerization, alkylation, polymerization and so on with olefins as the reactant.

Various kinds of known catalytic reactors can be used for the catalytic conversion of methyl alcohol and/or dimethyl ether into lower olefins using the inventive aluminoborosilicate as the catalyst including fixed-bed, fluidized-bed and moving-bed reactors provided that the gaseous feed can be satisfactorily contacted with the solid catalyst.

The reaction conditions applicable to this process cover wide ranges For example, the reaction is performed at a temperature in the range from 300° to 650° C. or, preferably, from 500° to 600° C. under a total pressure of 0.1 to 100 atmospheres or, preferably 0.5 to 10 atmospheres keeping a weight-hours space velocity of 0.1 to 20 $hr^{-1}$ or, preferably, 1 to 10 $hr^{-1}$. The gaseous feed of methyl alcohol and/or dimethyl ether brought into contact with the catalyst may be diluted with steam or an inert gas such as nitrogen, argon and the like. The aluminoborosilicate as the catalyst preferably should have such a chemical composition that the atomic ratio of the alkaline earth metal to aluminum is 0.4 to 8, molar ratio of $SiO_2:B_2O_3$ is 1 to 100 and molar ratio of $B_2O_3:Al_2O_3$ is 0.08 to 80.

The gaseous outflow in the reaction is composed of water vapor, product olefins, unreacted reactant or reactants and, when used, carrier gas and the proportion of the desired products, i.e. lower olefins such as ethylene and propylene, in the overall hydrocarbons can be increased by appropriately controlling the reaction conditions. The products of lower olefins can be separated and purified from the other ingredients of the gaseous outflow by a known method. In the calculation of the selectivity of the catalytic reaction, the dimethyl ether produced from methyl alcohol as an intermediate can be included in the unreacted starting material because dimethyl ether is also used as a starting material.

The catalytic reaction for the synthesis of lower olefins from methyl alcohol and/or dimethyl ether using the inventive aluminoborosilicate catalyst is an exothermic reaction so that the temperature of the catalyst bed is increased spontaneously as the reaction is continued. Therefore, no particular difficulties are encountered in keeping the catalyst bed at the above mentioned high temperature from the standpoint of energy consumption or it is rather an easier matter to keep and control the catalyst bed at the high temperature than at a lower temperature in addition to the advantage that a smaller reactor can be used by virtue of the higher reaction velocity at the high reaction temperature than at lower temperatures. A temperature higher than 650° C., however, is practically not feasible due to the problem in the serviceable life of the material of the reactor which is typically a stainless steel incapable of withstanding prolonged service at higher temperatures. Moreover, the crystalline structure of the catalyst may eventually be destroyed at high temperatures by the steam contained in the gaseous mixture. These situations are the reasons for the upper limit of 650° C. as the reaction temperature. In the alkaline earth-containing aluminoborosilicate of the invention, the boron ions along with the aluminum ions are the substituents for a part of the silicon atoms forming the principal constituents of the crystalline skeleton. This fact can be evidenced by the results of the X-ray diffractometry, determination of ammonia liberated by temperature elevation and quantitative determination of boron by the high-frequency plasma analysis described below.

In the first place, the X-ray diffraction diagram of the alkaline earth-containing aluminoborosilicate of the invention indicates that the lattice constant of the (804) planes is decreased to give an evidence that boron ions having a smaller ionic radius than aluminum ions are the substitutes for silicon atoms along with the aluminum ions.

The above mentioned conclusion is a result of the following X-ray diffractometric studies. Namely, a series of ZSM-5 type zeolites were prepared according to the procedure described in Example 3 or British Patent No. 1,402,981 with varied molar ratios of $SiO_2:Al_2O_3$ and each of them was intimately mixed with a fine powder of silicon having a purity of 99.99% as an internal standard An X-ray diffraction diagram was taken of each of the powdery mixtures, of which the diffraction angle of the line ascribable to the (804) planes of the zeolite appearing at $2\theta=$ca. 45° (Cu K$\alpha$) was accurately determined with reference to the diffraction line by the (220) planes of silicon appearing at $2\theta=47.3°$ as the standard. A comparison of the thus determined diffraction angles for the series of zeolites indicated that the diffraction angle $2\theta$ of the line by the (804) planes shifted toward lower angles as the molar ratio of $SiO_2$:$Al_2O_3$ decreased with an increased content of aluminum ions having a larger ionic radius than silicon. Accordingly, it was a due assumption that, when silicon atoms were replaced with boron ions having a smaller ionic radius, the diffraction angle of the line by the (804) planes of zeolites would shift toward higher angles evidencing the decrease in the lattice constant thereof.

Based on the above mentioned assumption, a comparative X-ray diffractometric test was undertaken of two samples, of which the first was a calcium-containing aluminosilicate prepared with molar ratios of $SiO_2:Al_2O_3$ of 100 and $CaO:SiO_2$ of 0.025 and the second was a calcium-containing aluminoborosilicate prepared in Preparation 1 described below using boric acid to give a molar ratio $SiO_2:B_2O_3$ of 10, the molar ratios of $SiO_2:Al_2O_3$ and $CaO:SiO_2$ being the same as above. The comparison of the $2\theta$ angles of the diffraction lines by the (804) planes of these two samples indicated a shift of the $2\theta$ angle of the latter sample to a larger angle of 45.24° from 45.02° of the former sample to give an evidence for the decrease in the lattice constant of the (804) planes by the substitution of boron ions having a smaller ionic radius than silicon for the silicon atoms in the zeolitic skeleton.

Figure 2:
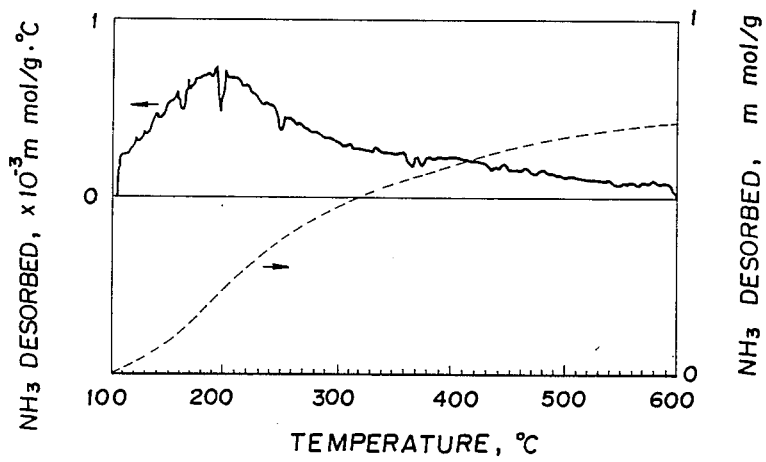
FIG. 2 is a graphic showing of the desorbed amount of ammonia adsorbed on the calcium-containing aluminoborosilicate obtained in Preparation 5 by heating as a function of temperature of desorption.
Figure 3:
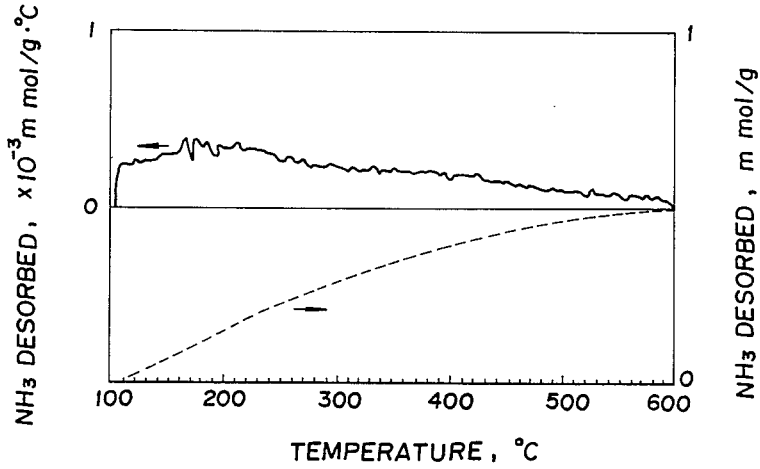
FIG. 3 is a graphic showing of the desorbed amount of ammonia adsorbed on the calcium-containing aluminosilicate obtained in Preparation 5 without using the boron source for comparative purpose by heating as a function of temperature of desorption.

In the second place, it is known that replacement of the [silicon atoms in the zeolitic skeleton with boron has an effect of increasing the amount of ammonia adsorption corresponding to the weak acid points at relatively low temperatures. In this regard, the calcium-containing aluminoborosilicate of the invention prepared in Preparation 5 described below could adsorb 0.21 m moles/g of ammonia at 100° C. as is shown in FIG. 2 while the amount of ammonia adsorption was 0.50 m moles/g on a calcium-containing aluminosilicate prepared with a formulation identical to that for the above excepting omission of the boron compound as is shown in FIG. 3 supporting the above mentioned general trend resulting from the substitution of boron ions for the silicon atoms as was also evidenced by the results of the high-frequency plasma analysis for the content of boron as shown in table 4 given below.

The alkaline earth-containing aluminoborosilicate of the invention exhibits unusual behavior in the adsorption of hydrocarbons. Namely, the aluminoborosilicate is capable of adsorbing paraffins of a linear-chained or slightly-branched molecular structure such as n-hexane and 3-methyl pentane among isomers of hexanes while 2,2-dimethyl butane cannot be adsorbed thereon.

Accordingly, it is a conclusion that the above described alkaline earth-containing aluminoborosilicate of the invention is a novel zeolitic material characterized also by the pore diameter which is intermediate between the small pore diameter in small-pore zeolites such as erionite and offretite and the large pore diameter of the X- and Y-type faujasite zeolites. The alkaline earth-containing aluminoborosilicate of the present invention is outstandingly heat-resistant and the crystalline structure is little affected even by a heat treatment at a temperature up to 900 ° C. These unique properties are very advantageous in the application of the inventive aluminoborosilicate as a catalyst or adsorbent used in the petroleum refining processes and petrochemical industries which is not rarely subjected to a pre-treatment or regeneration by heating at elevated temperatures. In addition to this advantage owing to the heat stability, the inventive aluminoborosilicate is of course excellent as a solid catalyst for the preparation of lower olefins such as ethylene and propylene in a high yield from methyl alcohol and/or dimethyl ether in respect of the selectivity and activity with suppression of the undesirable side reactions to convert the starting material into carbon monoxide or methane over a prolonged period of time with greatly decreased deposition of carbonaceous materials thereon.

In the following, descriptions are given of the preparation and catalytic performance of the alkaline earth-containing aluminoborosilicates of the invention in more detail by way of examples, which should not be construed to be limitative of the scope of the invention in any way.

Preparation 1.

An aqueous gelled mixture was prepared by dissolving 1.34 g of calcium acetate $Ca(CH_3COO)_2H_2O$, abridged as $Ca(OAc)_2 \cdot H_2O$ hereinbelow, 8.11 g of tetra(n-propyl) ammonium bromide, referred to as TPABr hereinbelow, 2.28 g of aluminum nitrate nonahydrate $Al(NO_3)_3 \cdot 9H_2O$, 3.77 g of boric acid $H_3BO_3$ and 1.71 g of sodium hydroxide NaOH successively in this order in 170 g of water followed by the addition of 60 g of a colloidal silica (Cataloid SI-30, a product by Shokubai Kasei Co. containing 30–31% of $SiO_2$ and 0.37–0.46% of $Na_2O$) under thorough agitation.

The aqueous gelled mixture was introduced into an autoclave of 300 ml capacity and subjected to a hydrothermal treatment at 160° C. for 16 hours under a spontaneously produced pressure with the stirrer driven at 500 rpm. The mixture after the reaction was centrifugally separated into solid and liquid and the solid was thoroughly washed with water and dried at 120 ° C. for about 7 hours.

The solid material thus obtained was then calcined in air at 500° C. for about 5 hours to give a zeolitic material of Na form. A 1.0 g portion of this zeolite was dispersed in 13 ml of a 5% aqueous solution of ammonium chloride and stirred for 1 hour at room temperature followed by thorough washing with water, drying at 120° C. and calcined at 500° C. in air for about 3 hours into a calcium-containing aluminoborosilicate of H form of which the microcrystallites had a diameter of about 0.2 μm and the specific surface area determined by the BET method was 307.6 m²/g. The results of the X-ray fluorescence spectrophotometric analysis on the weight basis were: 0.20% of $B_2O_3$; 0.064% of CaO; 98.2 of the molar ratio $SiO_2:Al_2O_3$; and trace of $Na_2O$. An X-ray diffraction diagram of the Na form material obtained by use of an X-ray source of Cu Kα line is shown in FIG. 1, and the lattice constants d in angstrom unit and the relative intensities of the diffraction lines corresponding thereto determined from the diagram were as follows, the relative intensity being given in brackets: 11.06 (100); 9.95 (68.3); 7.42 (2.5); 6.66 (7.1); 6.31 (14.7); 5.95 (19.8); 5.66 (11.9); 5.53 (14.3); 5.33 (4.0); 5.00 (7.9); 4.58 (6.0); 4.34 (9.5); 4.24 (11.9); 3.97 (8.7); 3.83 (81.0); 3.70 (43.7); 3.63 (23.5); 3.45 (7.5); 3.43 (8.7); 3.29 (9.9); 3.23 (5.2); 3.03 (7.9); 2.97 (12.7); 2.00 (7.1); and 1.98 (7.1).

Preparations 2 to 17.

The synthetic procedure in each of Preparations 2 to 14 was substantially the same as in Preparation 1 described above except that the amounts of the respective reactants were as summarized in Table 1 and the conditions were modified in some respects as described below. The amount of TPABr was always 8.11 g in each of Preparations 2 to 17 and the temperature of the hydrothermal reaction was always 160° C. excepting Preparations 10 and 11 as mentioned below. Table 1 also includes the data in Preparation 1. The X-ray diffraction diagram of each of the thus prepared alkaline earth-containing aluminoborosilicates in the Na form was substantially identical with that in Preparation 1.

In Preparations 7 to 9 and 11 to 14, the conversion of the Na form into the hydrogen form was performed by dispersing and agitating 1.0 g of the Na form material in 13 ml of a 0.6N hydrochloric acid for 24 hours at room temperature in place of calcination of the ammonium form.

In Preparations 10 and 11, the hydrothermal reaction of the aqueous reaction mixture was performed under normal pressure at 100° C. in a quartz glass-made reaction vessel in place of the autoclave.

Preparations 15 to 17 were undertaken for comparative purpose to prepare ZSM-5 type zeolites of the hydrogen form in the same synthetic procedure as in the preceding Preparations excepting omission of boric acid and calcium acetate. The amounts of other reactants in the reaction mixture are shown in Table 1.

In Preparation 16, the aluminosilicate in the hydrogen form was subjected to ion exchange with calcium ions according to a conventional procedure. Thus, a 5.0 g portion of the alumino-silicate in the hydrogen form was added to 40 ml of a 1N aqueous solution of calcium chloride and the dispersion was agitated at 80° C. in a flask equipped with a reflux condenser. After about 3 hours of heating, the liquid portion of the mixture was discarded by decantation and 30 ml of a fresh solution of calcium chloride were added thereto to resume heating under agitation. This procedure was repeated 20 times and the zeolite was washed with water repeatedly until no chlorine ions were detected in the washings, filtered, dried and calcined at 500° C. for 3 hours to give a ZSM-5 type zeolite ion-exchanged with calcium. The results of the X-ray fluorescence spectrophotometric analysis indicated that 45% of the hydrogen ions in the starting zeolite had been ion-exchanged with calcium.

In Preparation 17, calcium ions were introduced into the zeolite of the hydrogen form according to the procedure described in Japanese Patent Kokai No. 56-133223. Thus, a 6.0 g portion of the zeolite was added to an aqueous solution of 4.5 g of calcium acetate dissolved in 20 ml of water and the dispersion was agitated at 80° C. for 4 hours in a flask equipped with a reflux condenser and the zeolite was recovered by filtration, washed with water, dried and calcined at 500° C. for 3 hours.

Table 2 below shows the results of the X-ray fluorescence spectrophotometric analysis and the determination of the specific surface area by the BET method for each of the alkaline earth-containing containing aluminoborosilicates in the hydrogen form obtained in Preparations 2 to 4, 6, 8 and 12 to 14 together with the data in Preparation 1. MO in the table denotes the alkaline earth oxide which may be CaO, SrO, MgO or BaO. According to the microphotograph obtained using a scanning electron microscope indicated that the aluminoborosilicate prepared in Preparation 2 was a microcrystalline zeolite having a crystallite size of about 0.3 μm.

FIGS. 2 and 3 are each a thermogravimetric diagram showing the desorbed amount of ammonia from the zeolitic materials in the ammonium form prepared in Preparations 5 and 15, respectively, at a rate of temperature elevation of 5° C./minute with the increasing temperature taken as the abscissa.

EXAMPLES 1 TO 14 AND COMPARATIVE EXAMPLES 1 TO 3.

Each of the zeolites, i.e. aluminoborosilicate or aluminosilicate, in the powdery form obtained in Preparations 1 to 17 was pelletized by compression molding under a pressure of 400 kg/cm² and the pellets were crushed to give granules having a particle size distribution of 12 to 14 mesh after classification by sieving. The granules in a volume of 2 ml were taken in a quartz glass-made reaction tube of 10 mm inner diameter and a gaseous mixture of methyl alcohol vapor and argon gas as the internal standard was passed through the tube containing the zeolite as the catalyst and kept at a temperature of 320° to 600° C. under approximately normal pressure. The zeolites used in Examples 1 to 14 were each the aluminoborosilicate prepared in Preparations 1 to 14, respectively, and those used in Comparative Examples 1 to 3 were each the aluminosilicate prepared in Preparations 15 to 17, respectively. The methyl alcohol vapor was obtained from an evaporator in which liquid methyl alcohol was vaporized at a rate of 4 ml/hour while the argon gas was mixed with the methyl alcohol vapor at a rate of 40 ml/hour. The reaction temperature at the start of the reaction was 320° C. and increased stepwise by 10° to 40° C. in every 2 hours until the final temperature of about 600° C. was reached. Table 3 shows the molar ratios of $SiO_2:Al_2O_3$, $SiO_2:B_2O_3$ and $MO:SiO_2$ in each of the zeolites used in these Examples and Comparative Examples, M being the alkaline earth metal element.

The outflow gas out of the reaction tube after about 2 hours from the moment when the temperature of about 600° C. had been reached with establishment of the stationary state was gas-chromatographically analyzed to give the results shown in Table 4 below including the reaction temperature and selectivities of ethylene, propylene and butene calculated on the carbon base. The selectivity of $C'_2+C'_3$ means the sum of the selectivities of ethylene and propylene and $C'_2+C'_3'+C'_4$ means the sum of the selectivities of ethylene, propylene and butene. The effective conversion of the feed of methyl alcohol was 100% at the reaction temperature shown in Table 4 in each experiment except that the values in Comparative Examples 1, 2 and 3 at reaction temperatures of 558° C., 540° C. and 598° C., respectively, were 19.5%, 99.0% and 89.8%, respectively. The effective conversion in % here was calculated taking dimethyl ether as the unreacted starting material. Further, Table 5 to 16 show the details of the selectivity data at varied temperatures in Examples 2, 4, 5, 7, 8, 9, 10, 12, 13 and 14 and Comparative Examples 1 and 2, respectively, together with the data of methyl alcohol conversion and effective conversion.

As is understood from the results shown in Tables 4 to 16, the alkaline earth-containing aluminoborosilicates of the invention used in Examples 1 to 14 are superior as a catalyst of the reaction to the conventional zeolite catalysts used in the comparative examples in respects of the high yield of ethylene and propylene, high durability of the catalyst activity without degradation even at high temperatures, little formation of carbon monoxide, carbon dioxide and methane and small amounts of aromatics formed as the by-products presumably responsible for the formation of carbonaceous matters to be deposited on the catalyst.

TABLE 3

| | | Composition, molar ratio | | | |
|---|---|---|---|---|---|
| | | $SiO_2:Al_2O_3$ | $SiO_2:B_2O_3$ | M | $MO:SiO_2$ |
| Example | 1 | 100 | 10 | Ca | 0.025 |
| | 2 | 100 | 20 | Ca | 0.025 |
| | 3 | 100 | 40 | Ca | 0.025 |
| | 4 | 100 | 80 | Ca | 0.025 |
| | 5 | 200 | 20 | Ca | 0.025 |
| | 6 | 200 | 20 | Ca | 0.025 |
| | 7 | 200 | 20 | Ca | 0.025 |
| | 8 | 400 | 20 | Ca | 0.025 |
| | 9 | 1000 | 20 | Ca | 0.025 |
| | 10 | 100 | 20 | Ca | 0.025 |
| | 11 | 100 | 40 | Ca | 0.025 |
| | 12 | 100 | 20 | Sr | 0.025 |
| | 13 | 200 | 20 | Mg | 0.025 |
| | 14 | 100 | 20 | Ba | 0.007 |
| Comparative Example | 1 | 200 | — | — | — |
| | 2 | 300 | — | Ca | Ion-exchanged |
| | 3 | 80 | — | Ca | Ion-exchanged |

TABLE 4

| | | Reaction temperature, °C. | Selectivity, % | | | | |
|---|---|---|---|---|---|---|---|
| | | | $C_2H_4$ | $C_3H_6$ | $C_4H_8$ | $C'_2+C'_3$ | $C'_2+C'_3+C'_4$ |
| Example | 1 | 538 | 19.9 | 40.2 | 18.1 | 60.1 | 78.2 |
| | 2 | 548 | 16.6 | 42.9 | 18.8 | 59.5 | 78.3 |
| | | 598 | 21.6 | 41.0 | 14.5 | 62.6 | 77.1 |
| | 3 | 538 | 16.3 | 43.7 | 19.9 | 60.0 | 79.9 |
| | | 598 | 21.1 | 41.5 | 14.4 | 62.6 | 77.0 |
| | 4 | 538 | 17.3 | 44.0 | 19.7 | 61.3 | 81.0 |
| | | 598 | 23.0 | 42.1 | 14.4 | 65.1 | 79.5 |
| | 5 | 558 | 14.0 | 45.2 | 21.3 | 59.2 | 80.5 |
| | | 597 | 18.7 | 44.7 | 17.6 | 63.4 | 81.0 |
| | 6 | 558 | 17.3 | 43.4 | 17.9 | 60.7 | 78.6 |
| | | 598 | 20.2 | 41.7 | 11.7 | 61.9 | 73.6 |
| | 7 | 558 | 15.1 | 45.3 | 19.5 | 60.4 | 79.9 |
| | | 598 | 19.7 | 44.8 | 16.8 | 64.5 | 81.3 |
| | 8 | 598 | 15.8 | 44.6 | 17.4 | 60.4 | 77.8 |
| | 9 | 598 | 10.7 | 43.7 | 18.6 | 54.4 | 73.0 |
| | 10 | 538 | 18.3 | 43.1 | 19.0 | 61.4 | 80.4 |
| | | 597 | 23.4 | 41.9 | 13.9 | 65.3 | 79.2 |
| | 11 | 558 | 18.1 | 43.5 | 17.7 | 61.6 | 79.3 |
| | 12 | 558 | 9.9 | 43.7 | 19.2 | 53.6 | 72.8 |
| | | 598 | 13.5 | 42.1 | 16.8 | 55.6 | 72.4 |
| | 13 | 539 | 13.7 | 32.3 | 14.8 | 46.0 | 60.8 |
| | 14 | 538 | 15.4 | 31.5 | 13.7 | 46.9 | 60.5 |
| Comparative Example | 1 | 500 | 14.9 | 29.5 | 11.4 | 44.4 | 55.8 |
| | | 558 | 5.0 | 2.6 | 0.4 | 7.6 | 8.0 |
| | 2 | 500 | 12.7 | 36.8 | 17.6 | 49.5 | 67.1 |
| | | 540 | 11.7 | 29.2 | 8.8 | 40.9 | 49.7 |
| | 3 | 539 | 13.8 | 18.1 | 10.1 | 31.9 | 42.0 |

TABLE 1

| Preparation No. | Colloidal silica, g | $Al(NO_3)_3 \cdot 9H_2O$, g | $H_3BO_3$, g | NaOH, g | Salt of alkaline earch metal | | Water, g | Time, hours |
|---|---|---|---|---|---|---|---|---|
| | | | | | Kind | g | | |
| 1 | 60 | 2.28 | 3.77 | 1.71 | $Ca(OAc)_2 \cdot H_2O$ | 1.34 | 170 | 16 |
| 2 | 60 | 2.28 | 1.88 | 1.71 | $Ca(OAc)_2 \cdot H_2O$ | 1.34 | 170 | 16 |
| 3 | 60 | 2.28 | 0.94 | 1.71 | $Ca(OAc)_2 \cdot H_2O$ | 1.34 | 170 | 16 |
| 4 | 60 | 2.28 | 0.47 | 1.71 | $Ca(OAc)_2 \cdot H_2O$ | 1.34 | 170 | 16 |
| 5 | 60 | 1.14 | 1.88 | 1.32 | $Ca(OAc)_2 \cdot H_2O$ | 1.34 | 170 | 16 |
| 6 | 120 | 2.28 | 3.76 | 4.96 | $Ca(OAc)_2 \cdot H_2O$ | 2.68 | 1.37 | 16 |
| 7 | 60 | 1.14 | 1.88 | 1.33 | $Ca(OAc)_2 \cdot H_2O$ | 1.34 | 170 | 16 |
| 8 | 120 | 1.14 | 3.76 | 4.60 | $Ca(OAc)_2 \cdot H_2O$ | 2.68 | 137 | 16 |
| 9 | 60 | 0.23 | 1.88 | 0.97 | $Ca(OAc)_2 \cdot H_2O$ | 1.34 | 170 | 16 |
| 10 | 60 | 2.28 | 1.88 | 2.99 | $Ca(OAc)_2 \cdot H_2O$ | 1.34 | 170 | 168 |
| 11 | 60 | 2.28 | 0.94 | 1.71 | $Ca(OAc)_2 \cdot H_2O$ | 1.34 | 170 | 336 |
| 12 | 120 | 4.56 | 3.76 | 4.47 | $Sr(OAc)_2 \cdot \frac{1}{2}H_2O$ | 3.26 | 137 | 16 |
| 13 | 120 | 2.28 | 3.76 | 4.96 | $Mg(OAc)_2 \cdot 4H_2O$ | 3.27 | 137 | 16 |
| 14 | 120 | 4.56 | 3.76 | 4.47 | $Ba(OAc)_2$ | 1.09 | 137 | 16 |
| 15 | 60 | 1.14 | — | 1.33 | — | — | 170 | 16 |
| 16 | 60 | 0.75 | — | 1.20 | — | — | 170 | 16 |
| 17 | 60 | 2.78 | — | 1.91 | — | — | 170 | 16 |

TABLE 2

| Preparation No. | Specific surface area, $m^2/g$ | Analitical value | | | | |
|---|---|---|---|---|---|---|
| | | $SiO_2:Al_2O_3$ molar ratio | B, % by weight | M, % by weight | M:Al | MO |
| 1 | 307.6 | 98.2 | 0.20 | 0.54 | 0.44 | CaO |
| 2 | 342.1 | 100.8 | 0.13 | 0.87 | 0.94 | CaO |
| 3 | 333.9 | 99.1 | 0.25 | 1.03 | 0.82 | CaO |
| 4 | 306.7 | 104.4 | 0.17 | 0.88 | 0.79 | CaO |
| 6 | 329.3 | 164.2 | 0.18 | 0.39 | 0.53 | CaO |
| 8 | 322.8 | 376.9 | 0.25 | 0.54 | 1.67 | CaO |
| 10 | 325.3 | 113.3 | 0.14 | 0.64 | 0.58 | CaO |
| 11 | 333.8 | 120.6 | 0.12 | 0.51 | 0.52 | CaO |
| 12 | 300.7 | 103.5 | 0.22 | 3.14 | 1.25 | SrO |
| 13 | 345.5 | 195.1 | 0.16 | 0.21 | 0.53 | MgO |
| 14 | 327.0 | 101.0 | 0.13 | 1.21 | 0.29 | BaO |
| 15 | 364.1 | 196.5 | 0 | 0 | 0 | — |
| 17 | 339.8 | 81.9 | 0 | 0.12 | 0.08 | CaO |

TABLE 4-continued

| Reaction temperature, °C. | Selectivity, % | | | | |
|---|---|---|---|---|---|
| | $C_2H_4$ | $C_3H_6$ | $C_4H_8$ | $C'_2 + C'_3$ | $C'_2 + C'_3 + C'_4$ |
| 598 | 7.3 | 7.2 | 1.3 | 14.5 | 15.8 |

TABLE 5
(Example 2)

| Reaction temperature °C. | | 439 | 499 | 538 | 548 | 558 | 598 |
|---|---|---|---|---|---|---|---|
| Conversion of methyl alcohol, % | | 91.5 | 100 | 100 | 100 | 100 | 100 |
| Effective conversion, % | | 83.9 | 100 | 100 | 100 | 100 | 100 |
| Selectivity, % | $CO + CO_2$ | 0 | 0 | 0.03 | 0.04 | 0.18 | 0.78 |
| | $CH_4$ | 0.36 | 0.41 | 0.72 | 0.89 | 0.99 | 2.29 |
| | $C_2H_4$ | 1.90 | 10.01 | 15.29 | 16.63 | 17.21 | 21.58 |
| | $C_2H_6$ | 0 | 0 | 0 | 0 | 0 | 0 |
| | $C_3H_6$ | 29.01 | 39.43 | 42.21 | 42.89 | 42.41 | 40.97 |
| | $C_3H_8$ | 0.39 | 1.09 | 1.05 | 1.02 | 0.96 | 0.81 |
| | $C_4H_8$ | 17.41 | 22.81 | 19.45 | 18.75 | 17.74 | 14.53 |
| | $i-C_4 + n-C_4$ | 2.78 | 1.93 | 1.37 | 1.22 | 1.10 | 0.79 |
| | $C_5H_{10}$ | 10.98 | 8.11 | 5.21 | 4.64 | 4.07 | 2.20 |
| | $C_5H_{12}$ | 0 | 0 | 0 | 0 | 0 | 0 |
| | B.T.X. | 1.87 | 2.55 | 4.16 | 4.98 | 5.59 | 9.93 |
| | Others | 35.30 | 13.66 | 10.50 | 8.94 | 9.74 | 6.12 |
| | $C'_2 + C'_3$ | 30.91 | 49.44 | 57.50 | 59.52 | 59.62 | 62.55 |
| | $C'_2 + C'_3 + C'_4$ | 48.32 | 72.25 | 76.95 | 78.27 | 77.36 | 77.08 |

TABLE 6
(Example 4)

| Reaction temperature °C. | | 440 | 499 | 538 | 548 | 558 | 598 |
|---|---|---|---|---|---|---|---|
| Conversion of methyl alcohol, % | | 85.5 | 100 | 100 | 100 | 100 | 100 |
| Effective conversion, % | | 62.3 | 100 | 100 | 100 | 100 | 100 |
| Selectivity, % | $CO + CO_2$ | 0 | 0 | 0 | 0 | 0.12 | 0.77 |
| | $CH_4$ | 0.41 | 0.37 | 0.67 | 0.81 | 0.90 | 2.32 |
| | $C_2H_4$ | 2.21 | 11.27 | 17.26 | 18.21 | 19.07 | 22.98 |
| | $C_2H_6$ | 0 | 0 | 0 | 0 | 0.39 | 0.51 |
| | $C_3H_6$ | 29.09 | 40.61 | 43.96 | 43.80 | 43.41 | 42.11 |
| | $C_3H_8$ | 0.31 | 1.16 | 1.17 | 1.14 | 1.08 | 0.93 |
| | $C_4H_8$ | 17.20 | 22.88 | 19.72 | 18.75 | 17.62 | 14.35 |
| | $i-C_4 + n-C_4$ | 2.43 | 1.92 | 1.43 | 1.28 | 1.16 | 0.86 |
| | $C_5H_{10}$ | 11.49 | 7.14 | 4.34 | 3.84 | 1.43 | 0.87 |
| | $C_5H_{12}$ | 0 | 0.69 | 0.69 | 0.62 | 0.53 | 0.23 |
| | B.T.X. | 1.84 | 2.96 | 4.85 | 5.35 | 5.95 | 10.36 |
| | Others | 35.01 | 10.98 | 5.91 | 6.21 | 8.34 | 3.73 |
| | $C'_2 + C'_3$ | 31.30 | 51.88 | 61.22 | 62.01 | 62.48 | 65.09 |
| | $C'_2 + C'_3 + C'_4$ | 48.50 | 74.76 | 80.94 | 80.76 | 80.10 | 79.44 |

TABLE 7
(Example 5)

| Reaction temperature °C. | | 439 | 499 | 537 | 548 | 558 | 597 |
|---|---|---|---|---|---|---|---|
| Conversion of methyl alcohol, % | | 81.3 | 100 | 100 | 100 | 100 | 100 |
| Effective conversion, % | | 0.2 | 100 | 100 | 100 | 100 | 100 |
| Selectivity, % | $CO + CO_2$ | | 0 | 0 | 0 | 0 | 0.20 |
| | $CH_4$ | | 0.64 | 0.62 | 0.68 | 0.72 | 1.66 |
| | $C_2H_4$ | | 5.78 | 10.79 | 12.34 | 14.02 | 18.74 |
| | $C_2H_6$ | | 0 | 0 | 0 | 0 | 0 |
| | $C_3H_6$ | | 39.91 | 43.72 | 44.45 | 45.18 | 44.68 |
| | $C_3H_8$ | | 0.66 | 0.83 | 0.85 | 0.85 | 0.78 |
| | $C_4H_8$ | | 23.04 | 22.71 | 22.04 | 21.26 | 17.58 |
| | $i-C_4 + n-C_4$ | | 1.93 | 1.44 | 1.29 | 1.17 | 0.88 |
| | $C_5H_{10}$ | | 11.64 | 7.65 | 6.63 | 5.66 | 1.36 |
| | $C_5H_{12}$ | | 0 | 0 | 0 | 0 | 0 |
| | B.T.X. | | 2.16 | 2.92 | 3.13 | 3.62 | 6.89 |
| | Others | | 14.23 | 9.33 | 8.59 | 7.53 | 7.23 |
| | $C'_2 + C'_3$ | | 45.69 | 54.51 | 56.79 | 59.20 | 63.42 |

TABLE 7-continued
(Example 5)

| | | | | | |
|---|---|---|---|---|---|
| $C'_2 + C'_3 + C'_4$ | 68.73 | 77.22 | 78.83 | 80.46 | 81.00 |

TABLE 8
(Example 7)

| Reaction temperature °C. | | 440 | 499 | 538 | 548 | 558 | 598 |
|---|---|---|---|---|---|---|---|
| Conversion of methyl alcohol, % | | 81.4 | 100 | 100 | 100 | 100 | 100 |
| Effective conversion, % | | 4.0 | 100 | 100 | 100 | 100 | 100 |
| Selectivity, % | $CO + CO_2$ | | 0 | 0 | 0 | 0 | 0.27 |
| | $CH_4$ | | 0.87 | 0.57 | 0.58 | 0.67 | 1.16 |
| | $C_2H_4$ | | 3.56 | 11.92 | 13.69 | 15.12 | 19.71 |
| | $C_2H_6$ | | 0 | 0 | 0 | 0 | 0 |
| | $C_3H_6$ | | 37.37 | 44.33 | 45.02 | 45.29 | 44.78 |
| | $C_3H_8$ | | 0.35 | 0.67 | 0.70 | 0.70 | 0.63 |
| | $C_4H_8$ | | 19.63 | 20.85 | 20.25 | 19.50 | 16.77 |
| | $i-C_4 + n-C_4$ | | 1.48 | 1.12 | 0.98 | 0.92 | 0.74 |
| | $C_5H_{10}$ | | 12.62 | 6.39 | 5.46 | 4.65 | 2.57 |
| | $C_5H_{12}$ | | 0.12 | 0.10 | 0.09 | 0.09 | 0 |
| | B.T.X. | | 1.32 | 2.35 | 2.48 | 2.98 | 5.65 |
| | Others | | 22.67 | 11.70 | 10.75 | 10.10 | 7.74 |
| | $C'_2 + C'_3$ | | 40.93 | 56.25 | 58.71 | 60.41 | 64.49 |
| | $C'_2 + C'_3 + C'_4$ | | 60.56 | 77.10 | 78.96 | 79.91 | 81.26 |

TABLE 9
(Example 8)

| Reaction temperature °C. | | 440 | 499 | 538 | 548 | 558 | 598 |
|---|---|---|---|---|---|---|---|
| Conversion of methyl alcohol, % | | 82.6 | 100 | 100 | 100 | 100 | 100 |
| Effective conversion, % | | 5.8 | 100 | 100 | 100 | 100 | 100 |
| Selectivity, % | $CO + CO_2$ | 1.43 | 0 | 0 | 0 | 0.04 | 0.10 |
| | $CH_4$ | 2.46 | 0.86 | 1.11 | 1.08 | 1.05 | 1.70 |
| | $C_2H_4$ | 0 | 3.05 | 8.14 | 9.91 | 11.28 | 15.75 |
| | $C_2H_6$ | 0 | 0 | 0 | 0 | 0 | 0 |
| | $C_3H_6$ | 1.89 | 36.02 | 42.92 | 44.00 | 44.64 | 44.60 |
| | $C_3H_8$ | 0 | 0.32 | 0.46 | 0.46 | 0.47 | 0.47 |
| | $C_4H_8$ | 0 | 19.27 | 20.35 | 20.27 | 19.84 | 17.36 |
| | $i-C_4 + n-C_4$ | 0 | 1.54 | 1.03 | 0.84 | 0.74 | 0.62 |
| | $C_5H_{10}$ | 0 | 12.88 | 9.07 | 7.69 | 6.64 | 3.56 |
| | $C_5H_{12}$ | 0 | 0 | 0 | 0 | 0 | 0 |
| | B.T.X. | 0 | 1.24 | 2.33 | 2.72 | 3.03 | 5.82 |
| | Others | 94.22 | 24.82 | 14.60 | 13.03 | 12.24 | 10.02 |
| | $C'_2 + C'_3$ | 1.89 | 39.07 | 51.06 | 53.91 | 55.92 | 60.35 |
| | $C'_2 + C'_3 + C'_4$ | 1.89 | 58.34 | 71.41 | 74.18 | 75.76 | 77.71 |

TABLE 10
(Example 9)

| Reaction temperature °C. | | 499 | 538 | 548 | 558 | 598 |
|---|---|---|---|---|---|---|
| Conversion of methyl alcohol, % | | 76.1 | 82.8 | 92.5 | 100 | 100 |
| Effective conversion, % | | 7.7 | 35.9 | 83.3 | 100 | 100 |
| Selectivity, % | $CO + CO_2$ | 32.01 | 16.61 | 4.18 | 2.04 | 1.17 |
| | $CH_4$ | 17.53 | 9.19 | 2.57 | 1.55 | 1.82 |
| | $C_2H_4$ | 0.87 | 0.75 | 2.90 | 4.75 | 10.67 |
| | $C_2H_6$ | 0 | 0 | 0.10 | 0.12 | 0 |
| | $C_3H_6$ | 0.47 | 14.70 | 29.18 | 37.87 | 43.72 |
| | $C_3H_8$ | 0 | 0.13 | 0.19 | 0.26 | 0.33 |
| | $C_4H_8$ | 0 | 5.05 | 16.71 | 18.73 | 18.58 |
| | $i-C_4 + n-C_4$ | 0 | 0.21 | 0.60 | 0.68 | 0.53 |
| | $C_5H_{10}$ | 0 | 8.60 | 13.35 | 13.84 | 8.08 |
| | $C_5H_{12}$ | 0 | 0 | 0 | 0 | 0 |
| | B.T.X. | 0 | 0.07 | 0.49 | 1.22 | 3.89 |
| | Others | 49.12 | 44.70 | 29.73 | 18.93 | 11.21 |
| | $C'_2 + C'_3$ | 1.34 | 15.45 | 32.08 | 42.62 | 54.39 |
| | $C'_2 + C'_3 + C'_4$ | 1.34 | 20.50 | 48.79 | 61.35 | 72.97 |

TABLE 11

(Example 10)

| | | | | | | | |
|---|---|---|---|---|---|---|---|
| Reaction temperature °C. | | 440 | 499 | 538 | 548 | 558 | 597 |
| Conversion of methyl alcohol, % | | 100 | 100 | 100 | 100 | 100 | 100 |
| Effective conversion, % | | 100 | 100 | 100 | 100 | 100 | 100 |
| Selectivity, % | $CO + CO_2$ | 0 | 0 | 0.00 | 0.00 | 0 | 0.54 |
| | $CH_4$ | 0.18 | 0.47 | 0.69 | 0.85 | 1.07 | 2.26 |
| | $C_2H_4$ | 5.94 | 13.10 | 18.34 | 19.09 | 19.84 | 23.44 |
| | $C_2H_6$ | 0 | 0 | 0 | 0.36 | 0.39 | 0.63 |
| | $C_3H_6$ | 30.37 | 39.93 | 43.05 | 43.32 | 43.48 | 41.87 |
| | $C_3H_8$ | 1.37 | 1.54 | 1.41 | 1.36 | 1.29 | 1.08 |
| | $C_4H_8$ | 26.50 | 22.54 | 18.99 | 18.11 | 17.33 | 13.86 |
| | $i-C_4 + n-C_4$ | 3.82 | 2.16 | 1.48 | 1.36 | 1.20 | 0.87 |
| | $C_5H_{10}$ | 9.73 | 6.52 | 1.74 | 1.54 | 1.34 | 1.77 |
| | $C_5H_{12}$ | 0 | 0 | 0 | 0 | 0 | 0 |
| | B.T.X. | 2.81 | 3.73 | 5.59 | 6.21 | 6.91 | 11.43 |
| | Others | 19.29 | 10.00 | 8.72 | 7.79 | 7.15 | 2.26 |
| | $C'_2 + C'_3$ | 36.31 | 53.03 | 61.39 | 62.41 | 63.32 | 65.31 |
| | $C'_2 + C'_3 + C'_4$ | 62.81 | 75.57 | 80.38 | 80.52 | 80.65 | 79.17 |

TABLE 12

(Example 12)

| | | | | | | | |
|---|---|---|---|---|---|---|---|
| Reaction temperature, °C. | | 439 | 499 | 538 | 548 | 558 | 598 |
| Conversion of methyl alcohol, % | | 81.1 | 100 | 100 | 100 | 100 | 100 |
| Effective conversion, % | | 32.2 | 100 | 100 | 100 | 100 | 100 |
| Selectivity, % | $CO + CO_2$ | 0 | 0.28 | 0.96 | 1.26 | 1.90 | 4.36 |
| | $CH_4$ | 1.11 | 0.67 | 1.41 | 1.75 | 1.59 | 2.49 |
| | $C_2H_4$ | 2.98 | 5.74 | 8.98 | 9.12 | 9.91 | 13.48 |
| | $C_2H_6$ | 0 | 0 | 0 | 0 | 0 | 0 |
| | $C_3H_6$ | 25.07 | 41.23 | 43.52 | 43.49 | 43.71 | 42.07 |
| | $C_3H_8$ | 0.23 | 0.60 | 0.59 | 0.54 | 0.52 | 0.48 |
| | $C_4H_8$ | 12.25 | 22.01 | 20.36 | 19.72 | 19.21 | 16.75 |
| | $i-C_4 + n-C_4$ | 1.67 | 1.51 | 1.00 | 0.90 | 0.80 | 0.63 |
| | $C_5H_{10}$ | 9.58 | 10.64 | 7.74 | 7.37 | 6.60 | 3.60 |
| | $C_5H_{12}$ | 0 | 0 | 0 | 0 | 0 | 0 |
| | B.T.X | 0.99 | 1.93 | 3.36 | 3.89 | 4.45 | 7.76 |
| | Others | 45.90 | 15.39 | 12.08 | 11.96 | 11.30 | 8.40 |
| | $C'_2 + C'_3$ | 28.05 | 46.97 | 52.50 | 52.61 | 53.62 | 55.55 |
| | $C'_2 + C'_3 + C'_4$ | 40.03 | 68.98 | 72.86 | 72.33 | 72.83 | 72.30 |

TABLE 13

(Example 13)

| | | | | | | | |
|---|---|---|---|---|---|---|---|
| Reaction temperature, °C. | | 439 | 499 | 539 | 548 | 558 | 598 |
| Conversion of methyl alcohol, % | | 100 | 100 | 100 | 100 | 88.3 | 80.1 |
| Effective conversion, % | | 100 | 00 | 100 | 100 | 63.8 | 33.6 |
| Selectivity, % | $CO + CO_2$ | 0 | 0 | 0.22 | 0.98 | 2.81 | 12.89 |
| | $CH_4$ | 1.48 | 3.81 | 6.45 | 8.67 | 16.08 | 42.26 |
| | $C_2H_4$ | 8.28 | 12.34 | 13.69 | 11.96 | 7.70 | 2.79 |
| | $C_2H_6$ | 0 | 0.42 | 0.61 | 0.51 | 0.59 | 1.04 |
| | $C_3H_6$ | 22.87 | 30.74 | 32.31 | 30.26 | 17.62 | 2.07 |
| | $C_3H_8$ | 3.47 | 2.68 | 1.84 | 1.22 | 0.60 | 0 |
| | $C_4H_8$ | 20.84 | 17.51 | 14.78 | 12.87 | 6.63 | 0.28 |
| | $i-C_4 + n-C_4$ | 5.73 | 2.55 | 1.46 | 0.97 | 0.49 | 0 |
| | $C_5H_{10}$ | 9.02 | 5.85 | 4.29 | 5.54 | 5.96 | 1.08 |
| | $C_5H_{12}$ | 0 | 0 | 0.14 | 0.11 | 0 | 0.28 |
| | B.T.X. | 9.22 | 10.72 | 12.80 | 12.96 | 9.79 | 0.29 |
| | Others | 19.11 | 13.39 | 11.39 | 13.93 | 31.72 | 37.03 |
| | $C'_2 + C'_3$ | 31.15 | 43.08 | 46.00 | 42.22 | 25.32 | 4.86 |
| | $C'_2 + C'_3 + C'_4$ | 51.99 | 60.59 | 60.78 | 55.09 | 42.94 | 5.14 |

TABLE 14

(Example 14)

| | | | | | | | |
|---|---|---|---|---|---|---|---|
| Reaction temperature, °C. | | 440 | 499 | 538 | 548 | 558 | 598 |
| Conversion of methyl alcohol, % | | 100 | 100 | 100 | 100 | 100 | 96.5 |
| Effective conversion, % | | 100 | 100 | 100 | 100 | 100 | 89.9 |
| Selectivity, % | $CO + CO_2$ | 0 | 0.20 | 0.95 | 1.51 | 3.61 | 11.69 |
| | $CH_4$ | 1.35 | 4.03 | 7.54 | 9.19 | 13.77 | 25.30 |
| | $C_2H_4$ | 8.57 | 14.03 | 15.37 | 14.17 | 11.98 | 6.78 |
| | $C_2H_6$ | 0.24 | 0.47 | 0.62 | 0.60 | 0.64 | 0.88 |
| | $C_3H_6$ | 23.22 | 30.86 | 31.49 | 31.55 | 27.69 | 14.67 |
| | $C_3H_8$ | 3.77 | 2.99 | 2.06 | 1.52 | 0.87 | 0.32 |
| | $C_4H_8$ | 20.94 | 17.07 | 13.67 | 13.21 | 10.69 | 5.04 |
| | $i-C_4 + n-C_4$ | 6.52 | 2.86 | 1.55 | 1.19 | 0.71 | 0.26 |
| | $C_5H_{10}$ | 8.96 | 5.70 | 3.41 | 3.27 | 3.61 | 4.91 |
| | $C_5H_{12}$ | 0 | 0.22 | 0.14 | 0.12 | 0.08 | 0 |
| | B.T.X. | 9.36 | 11.41 | 14.17 | 14.49 | 15.21 | 8.77 |
| | Others | 17.07 | 10.14 | 9.04 | 9.18 | 11.14 | 21.38 |
| | $C'_2 + C'_3$ | 31.79 | 44.89 | 46.86 | 45.72 | 39.67 | 21.45 |
| | $C'_2 + C'_3 + C'_4$ | 52.73 | 61.96 | 60.53 | 58.93 | 50.36 | 26.49 |

TABLE 15

(Comparative Example 1)

| | | | | | | |
|---|---|---|---|---|---|---|
| Reaction temperature, °C. | | 400 | 439 | 499 | 538 | 558 |
| Conversion of methyl alcohol, % | | 100 | 100 | 100 | 97.8 | 78.2 |
| Effective conversion, % | | 100 | 100 | 100 | 92.0 | 19.5 |
| Selectivity, % | $CO + CO_2$ | 0 | 0 | 0 | 0.99 | 8.27 |
| | $CH_4$ | 1.32 | 2.22 | 5.58 | 10.38 | 45.35 |
| | $C_2H_4$ | 6.92 | 10.07 | 14.94 | 12.55 | 4.95 |
| | $C_2H_6$ | 0.21 | 0.41 | 0.70 | 0.73 | 1.71 |
| | $C_3H_6$ | 16.68 | 23.32 | 29.45 | 23.18 | 2.64 |
| | $C_3H_8$ | 4.90 | 4.68 | 3.52 | 1.64 | 0 |
| | $C_4H_8$ | 12.11 | 13.25 | 11.35 | 7.54 | 0.38 |
| | $i-C_4 + n-C_4$ | 9.96 | 6.60 | 2.95 | 1.39 | 0 |
| | $C_5H_{10}$ | 7.22 | 5.26 | 1.81 | 3.20 | 0.82 |
| | $C_5H_{12}$ | 8.14 | 6.20 | 4.00 | 2.94 | 0.35 |
| | B.T.X. | 14.03 | 13.27 | 15.29 | 14.11 | 0.19 |
| | Others | 18.50 | 14.72 | 10.40 | 21.36 | 35.34 |
| | $C'_2 + C'_3$ | 23.60 | 33.39 | 44.39 | 35.73 | 7.59 |
| | $C'_2 + C'_3 + C'_4$ | 35.71 | 46.64 | 55.74 | 43.27 | 7.97 |

TABLE 16

(Comparative Example 2)

| | | | | | | |
|---|---|---|---|---|---|---|
| Reaction temperature, °C. | | 360 | 400 | 440 | 499 | 540 |
| Conversion of methyl alcohol, % | | 99.1 | 100 | 100 | 100 | 99.5 |
| Effective conversion, % | | 99.1 | 100 | 100 | 100 | 99.0 |
| Selectivity, % | $CO + CO_2$ | 0 | 0 | 0 | 0.06 | 1.51 |
| | $CH_4$ | 0.27 | 0.38 | 0.79 | 3.21 | 9.83 |
| | $C_2H_4$ | 9.80 | 6.72 | 8.13 | 12.69 | 11.70 |
| | $C_2H_6$ | 0.12 | 0.11 | 0.17 | 0.38 | 0.58 |
| | $C_3H_6$ | 11.19 | 18.30 | 27.63 | 36.75 | 29.20 |
| | $C_3H_8$ | 1.58 | 1.47 | 1.61 | 0.69 | 0 |
| | $C_4H_8$ | 13.21 | 17.01 | 19.84 | 17.58 | 8.77 |
| | $i-C_4 + n-C_4$ | 10.04 | 9.31 | 6.41 | 2.68 | 1.07 |
| | $C_5H_{10}$ | 5.23 | 5.10 | 4.99 | 1.84 | 2.43 |
| | $C_5H_{12}$ | 10.29 | 9.63 | 8.05 | 5.14 | 3.29 |
| | B.T.X. | 7.54 | 7.31 | 5.60 | 13.43 | 13.76 |
| | Others | 30.74 | 24.28 | 16.78 | 5.07 | 17.86 |
| | $C'_2 + C'_3$ | 20.99 | 25.02 | 35.76 | 49.44 | 40.90 |
| | $C'_2 + C'_3 + C'_4$ | 34.20 | 42.03 | 55.60 | 67.02 | 49.67 |

What is claimed is:

1. A method for the catalytic conversion of methyl alcohol or dimethyl ether into lower olefins having 2 to 4 carbon atoms in a molecule which comprises bringing the vapor of methyl alcohol or dimethyl ether at a temperature in the range from 300° to 650° C. into contact with an aluminoborosilicate containing an alkaline earth metal element represented by the chemical composition of the formula $aM^1_2O \cdot bM^2O \cdot Al_2O_3 \cdot dB_2O_3 \cdot cSiO_2 \cdot nH_2O$, in which $M^1$ is a monovalent atom selected from the group consisting of a hydrogen atom and atoms of alkali metals, $M^2$ is an atom of an alkaline earth metal, a is zero or a positive number not exceeding 2, b is a positive number in the range from 0.1 to 100, c is a positive number in the range from 12 to 3000, d is a positive number in the range from 0.06 to 120 and n is zero or a positive number not exceeding 30.

2. The method of the catalytic conversion of methyl alcohol or dimethyl ether into lower olefins having 2 to 4 carbon atoms in a molecule as claimed in claim 1 wherein the aluminoborosilicate is further characterized by an X-ray diffraction diagram having diffraction lines of strong intensity corresponding to the lattice constants of $11.15 \pm 0.15$ and $3.84 \pm 0.07$, diffraction lines of medium intensity corresponding to the lattice constants of $10.01 \pm 0.15$, $3.81 \pm 0.07$, $3.74 \pm 0.07$ and $3.70 \pm 0.07$ and diffraction lines of weak intensity corresponding to the lattice constants of $7.42 \pm 0.10$, $6.70 \pm 0.10$, $6.35 \pm 0.10$, $5.97 \pm 0.10$, $5.67 \pm 0.10$, $5.56 \pm 0.10$, $5.34 \pm 0.10$, $5.00 \pm 0.10$, $4.59 \pm 0.10$, $4.34 \pm 0.10$, $4.24 \pm 0.10$, $3.99 \pm 0.10$, $3.65 \pm 0.07$, $3.45 \pm 0.05$, $3.42 \pm 0.05$, $3.30 \pm 0.05$, $3.24 \pm 0.05$, $3.04 \pm 0.05$, $2.97 \pm 0.05$, $2.01 \pm 0.02$ and $1.99 \pm 0.02$, each lattice constant being in the angstrom unit.

3. The method for the catalytic conversion of methyl alcohol or dimethyl ether into lower olefins having 2 to 4 carbon atoms in a molecule as claimed in claim 1 wherein c is in the range from 40 to 1000.

4. The method for the catalytic conversion of methyl alcohol or dimethyl ether into lower olefins having 2 to 4 carbon atoms in a molecule as claimed in claim 1 wherein the temperature is in the range from 500° to 600° C.

* * * * *